(12) United States Patent
Hakkens et al.

(10) Patent No.: US 11,213,275 B2
(45) Date of Patent: Jan. 4, 2022

(54) WEARABLE ULTRASOUND PATCH AND APPLICATION METHOD OF SUCH A PATCH

(71) Applicant: KONINKLIJKE PHILIPS N.V., Eindhoven (NL)

(72) Inventors: Franciscus Johannes Gerardus Hakkens, Eersel (NL); Lucas Johannes Anna Maria Beckers, Veldhoven (NL); Edward Theodorus Maria Berben, Herten (NL)

(73) Assignee: KONINKLIIKE PHILIPS N.V., Eindhoven (NL)

( * ) Notice: Subject to any disclaimer, the term of this patent is extended or adjusted under 35 U.S.C. 154(b) by 61 days.

(21) Appl. No.: 16/637,013

(22) PCT Filed: Aug. 8, 2018

(86) PCT No.: PCT/EP2018/071504
§ 371 (c)(1),
(2) Date: Feb. 6, 2020

(87) PCT Pub. No.: WO2019/030282
PCT Pub. Date: Feb. 14, 2019

(65) Prior Publication Data
US 2020/0163647 A1 May 28, 2020

(30) Foreign Application Priority Data
Aug. 8, 2017 (EP) ..................................... 17185370
Sep. 19, 2017 (EP) ..................................... 17191725

(51) Int. Cl.
*A61B 8/00* (2006.01)

(52) U.S. Cl.
CPC .......... *A61B 8/4281* (2013.01); *A61B 8/4236* (2013.01)

(58) Field of Classification Search
CPC ............................ A61B 8/4236; A61B 8/4281
See application file for complete search history.

(56) References Cited

U.S. PATENT DOCUMENTS

| 5,265,614 A | 11/1993 | Hayakawa et al. |
| 2006/0015058 A1 | 1/2006 | Kellogg et al. |

(Continued)

FOREIGN PATENT DOCUMENTS

| EP | 0331348 A1 | 9/1989 | |
| WO | 2011163570 A | 12/2011 | |
| WO | WO-2016207889 A1 * | 12/2016 | ........... A61B 8/4236 |

OTHER PUBLICATIONS

International Search Report and Written Opinion for International Application No. PCT/EP2018/071504, filed Aug. 8, 2018, 16 pages.

*Primary Examiner* — Boniface N Nganga (57) ABSTRACT

A wearable patch (10) is disclosed comprising an ultrasound transducer (30) mounted on the patch and a fluid reservoir (50) for containing a coupling agent (60) for the ultrasound transducer, said fluid reservoir being delimited by a portion (20) of the patch and a seal ring (40) extending from the patch, said seal ring surrounding the ultrasound transducer and comprising a plurality of fluid conduits (43, 45) extending from the fluid reservoir at least partially through the seal ring. Also disclosed are a wearable patch kit, assembly and application method.

11 Claims, 6 Drawing Sheets

(56) References Cited

U.S. PATENT DOCUMENTS

| | | | |
|---|---|---|---|
| 2008/0200810 A1* | 8/2008 | Buchalter | A61B 8/4236 600/459 |
| 2010/0076315 A1 | 3/2010 | Erkamp et al. | |
| 2011/0218418 A1* | 9/2011 | Green | A61B 8/4438 600/386 |
| 2012/0277640 A1 | 11/2012 | Lewis, Jr. et al. | |
| 2013/0237826 A1 | 9/2013 | Levien | |
| 2013/0289411 A1* | 10/2013 | Barnard | A61B 8/42 600/459 |
| 2014/0276048 A1 | 9/2014 | Kiley et al. | |

* cited by examiner

WEARABLE ULTRASOUND PATCH AND APPLICATION METHOD OF SUCH A PATCH

RELATED APPLICATIONS

This application is the U.S. National Phase application under 35 U.S.C. § 371 of International Application No. PCT/EP2018/071504, filed on Aug. 8, 2018, which claims priority to and the benefit of European Application No. 17191725.5, filed Sep. 19, 2017 and European Application No. 17185370.8, filed Aug. 8, 2017. These applications are hereby incorporated by reference herein.

FIELD OF THE INVENTION

The present invention relates to a wearable patch comprising an ultrasound transducer mounted on the patch and a fluid reservoir for containing a coupling agent for the ultrasound transducer.

The present invention further relates to a wearable patch assembly including such a wearable patch.

The present invention further relates to a wearable patch kit including such a wearable patch.

The present invention further relates to a method of applying such a wearable patch to a patient's skin region.

BACKGROUND OF THE INVENTION

Ultrasound imaging is an increasingly important diagnostic tool. In addition to high resolution imaging in hospitals and other medical practices, ultrasound imaging is more increasingly being used for patient monitoring over a prolonged period of time. In such a scenario, the patient typically wears a patch including an ultrasound transducer comprising one or more ultrasound transducer cells, which transducer is used to monitor a particular part of the patient's anatomy over such a time period.

The use of such wearable ultrasound patches for instance is contemplated for haemodynamic monitoring, in which parameters such as blood flow, pulse pressure, pulse wave velocity, cardiac output and cross-sectional dimensions of arteries may be monitored, bladder monitoring, e.g. within the clinical settings of a hospital, in which patient urine production and hydration rates may be monitored, coronary chronic total inclusion (CTO) monitoring to visualize large CTOs (>10 cm) that cannot be visualized using contrast-enhanced fluoroscopy and vascular access monitoring for the purpose of ultrasound-based diagnosis and treatment of peripheral diseases. Other applications of such longer-term ultrasound patient monitoring will be apparent to the skilled person.

As is well-known per se, in order to achieve a good acoustic coupling between the ultrasound transducer and the patient's body, a coupling agent, i.e. fluid, such as an ultrasound conductive gel typically is applied between the ultrasound transducer and the patient's body. During application of such an ultrasound transducer to the patient's body, pressure is applied to evacuate air bubbles from the coupling agent in order to establish the desired acoustic contact. The duration of ultrasound investigations in a clinical setting such as a hospital is relatively short, e.g. 5-15 minutes, which means that the coupling agent does not have time to dry out or otherwise degrade.

Such a coupling agent is equally desirable when applying a wearable ultrasound patch to a patient's body in order to establish the desired acoustic coupling between the patch and the patient's body. However, the use of a coupling agent in this context is not without challenges. Firstly, care has to be taken that the coupling agent does not interfere with the adhesion of the patch to the patient's body in case of an adhesive patch. Moreover, degradation of the coupling agent over the period during which the patch is worn by the patient must be prevented as much as possible.

Further requirements are that the positioning of the patch should be straightforward, in particular its repositioning in case the patch initially was placed in a sub-optimal location on the patient's skin, and air evacuation from the coupling agent should be easily achievable. The latter is not straightforward as limited amounts of the coupling agent should be used to avoid interference with adhesive layers of the patch (if present), but this brings about the risk of insufficient coupling agent remaining in between the patch and the patient's body when pressure is applied to the patch to evacuate such air bubbles.

US 2012/0277640 A1 discloses ultrasound coupling device for use an ultrasound transducer. The coupling device includes a coupling compartment comprising a chamber having a continuous side wall and an opening on a first end. The continuous side wall is configured to hold a low-profile ultrasound transducer within the chamber so that a front ultrasound emitting surface of the low-profile ultrasound transducer faces outward toward the chamber opening. The front ultrasound emitting surface is configured to control the direction and wave pattern of ultrasonic energy emitted from the transducer. The continuous side wall is also configured to hold a quantity of an ultrasound conductive medium within the chamber and is operative to keep the ultrasound conductive medium in simultaneous contact with a surface of a subject and with at least a portion of the front ultrasound emitting surface of the transducer. The ultrasound coupling device further includes a semi-permeable membrane configured to cover the opening at the first end of the chamber. The membrane is effective to allow the ultrasound conductive medium to be released from the first end of the coupling compartment when pressure is applied to semi-permeable membrane, e.g. by a subject manually pressing down on the ultrasound coupling device.

A drawback of this solution is that any excess ultrasound conductive medium must be forced from in between the ultrasound transducer and the patient's body past the continuous side wall, which can disturb the contact of this side wall to the patient's body. This therefore makes the robust positioning of such an ultrasound coupling device on the patient's body rather challenging.

SUMMARY OF THE INVENTION

The present invention seeks to provide a wearable patch comprising an ultrasound transducer mounted on the patch and a fluid reservoir for containing a coupling agent for the ultrasound transducer that facilitates easy (re)positioning of the patch on a patient's body.

The present invention further seeks to provide a wearable patch assembly including such a wearable patch.

The present invention further seeks to provide a wearable patch kit including such a wearable patch.

The present invention further seeks to provide a method of applying such a wearable patch to a patient's skin region.

According to an aspect, there is provided a wearable patch suitable for an ultrasound transducer to be mounted on the patch, said patch comprising a fluid reservoir for containing a coupling agent for the ultrasound transducer, said fluid reservoir being delimited by a portion of the patch and a seal ring extending from the patch, said seal ring surrounding the ultrasound transducer, when it is mounted on the patch, and arranged to be in contact with a part of a patient's body, when the wearable patch is secured to said part of the patient's body, wherein said seal ring comprises a plurality of fluid conduits extending from the fluid reservoir at least partially through the seal ring.

The provision of a seal ring, which extends from the patch towards a skin of the patient around the ultrasound transducer and comprises fluid conduits extending from the fluid reservoir provides a volume within the seal ring into which the coupling agent can expand when pressure is applied to the wearable patch when bringing the patch into contact with a skin region of the patient. This hermetically seals the seal ring, thereby protecting the coupling agent in the fluid reservoir from degradation over time in the sense that the rate of such degradation is at least significantly reduced due to the small contact area between the coupling agent and air in the seal ring. Moreover, a good contact between the seal ring and the skin region of the patient can be achieved in this manner due to the fact that the coupling agent is not forced underneath the seal ring when applying such pressure, i.e. in between the seal ring and the skin region of the patient, such that readjustment of the position of the wearable patch can be achieved in a straightforward manner. In other words, the wearable patch can be easily repositioned prior to permanently affixing the wearable patch to the patient due to the fact that the coupling agent is not lost from the wearable patch but instead is stored in the fluid conduits such that the wearable patch may be moved around without having to reapply the coupling agent after having exerted pressure on the wearable patch in an initial location, i.e. an initial skin region, on the body of the patient.

In a separate embodiment, the wearable patch can also include the ultrasound transducer, which may be either permanently or reversibly mounted on the patch.

The seal ring preferably is flexible in order to allow compression of the seal ring in order to establish an intimate contact between the wearable patch and the skin region of the patient.

In a particularly advantageous embodiment, the seal ring is made of a porous material such as a porous foam, the pores of said porous material defining the plurality of fluid conduits. Such an open structured material provides a particularly large fluid storage volume in which excess coupling agent can be evacuated into from the fluid reservoir, e.g. when applying pressure to the wearable patch. Any suitable foam may be used for this purpose, such as for example a polymer foam selected from polyurethane, polystyrene, polyethylene, silicone, polyvinylchloride or any other suitable polymer foam.

The pores of such a material may be open pores, i.e. pores fully extending through the seal ring or alternatively may be closed pores, i.e. porous only partially extending through the seal ring. In the latter scenario, the seal ring typically further comprises at least one vent channel extending from the fluid reservoir through the seal ring through which air can escape from the fluid reservoir, such that air bubbles can be evacuated therefrom when pressing the wearable patch against the skin region of the patient.

However, it should be understood that the seal ring is not necessarily made of a porous material. It is equally feasible that the seal ring is made of a non-porous material in which a plurality of fluid conduits such as vent channels are formed extending through the non-porous material in order to facilitate the evacuation of air and excess coupling agent from the fluid reservoir as explained above.

The wearable patch in some embodiments may be an adhesive patch to facilitate attachment of the wearable patch to a skin region of the patient. In such embodiments, the patch may have a central region carrying the ultrasound transducer and the seal ring, and an outer region surrounding the central region, wherein at least the outer region carries an adhesive. This has the advantage that the seal ring can be positioned on a body region of the patient without necessarily adhering the wearable patch to this body region, such that the wearable patch can be easily repositioned if necessary.

Alternatively or additionally, a surface portion of the seal ring for contacting the skin of a wearer of the patch carries an adhesive. This may obviate the need for an adhesive on the wearable patch surface or alternatively in case of the wearable patch also carrying an adhesive may further strengthen the adhesive bond between the wearable patch and the skin region of the patient to which the patch is applied.

Any suitable adhesive may be used for this purpose. Specifically mentioned is a pressure-sensitive adhesive, which can further assist in preventing the premature adhesion of the wearable patch to a particular skin region of the patient as the adhesion only is activated once a certain pressure is applied to the wearable patch in order to secure the patch against the skin region of the patient.

It should nevertheless be further understood that the wearable patch is not necessarily adhesive. Alternatively or additionally, the wearable patch may further comprise a strap for securing the patch to a part of a patient's body.

According to another aspect, there is provided a wearable patch assembly comprising the wearable patch according to any of the herein described embodiments and a control module attachable to the ultrasound transducer through a cable or wire, said control module comprising circuitry for controlling the operation of the ultrasound transducer and/or for processing the ultrasound images captured with the ultrasound transducer.

The functions of the controlling the operation of the ultrasound transducer and for the processing of the ultrasound images captured with the ultrasound transducer can be performed by different circuitry units, which can be physically located in separate devices. For example, a housing of the patch may comprise the circuitry part performing the operation controlling of the ultrasound transducer, while the circuitry part of the controlling module performing the processing of the ultrasound images captured with the ultrasound transducer may by realised at a distant server, whereto the ultrasound image data captured by the transducer are transmitted (for example, using a wireless communication module of the control module).

According to yet another aspect, there is provided a wearable patch kit comprising the wearable patch according to any of the herein described embodiments and a container containing the coupling agent for the ultrasound transducer.

According to still another aspect, there is provided a method of applying the wearable patch of any of the herein described embodiments to a skin region of a patient, the method comprising filling the fluid reservoir of the wearable patch with a coupling agent; positioning the filled wearable patch onto the skin region; and applying pressure to the wearable patch such that the seal ring contacts (by surrounding) a part (the skin region) of the patient's body thereby enabling air bubbles and excess coupling agent in the fluid reservoir to be forced into the plurality of fluid conduits. With this method, a durable high-quality acoustic coupling between the ultrasound transducer of the wearable patch and the skin region of the patient can be achieved in a straightforward manner.

In a separate embodiment, the method further comprises mounting of the ultrasound transducer (30) on the wearable patch.

In an embodiment, the method further comprises capturing at least one image with the ultrasound transducer positioned (together with the patch) on said skin region; and adjusting said positioning based on the captured at least one image. Due to the presence of the seal ring including the fluid conduits around the ultrasound transducer, such repositioning can be achieved without having to reapply coupling agent to the ultrasound transducer such that on the basis of the images captured with the ultrasound transducer the optimal placement of the wearable patch can be found prior to having to adhere or otherwise attach the wearable patch to the patient.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 1:
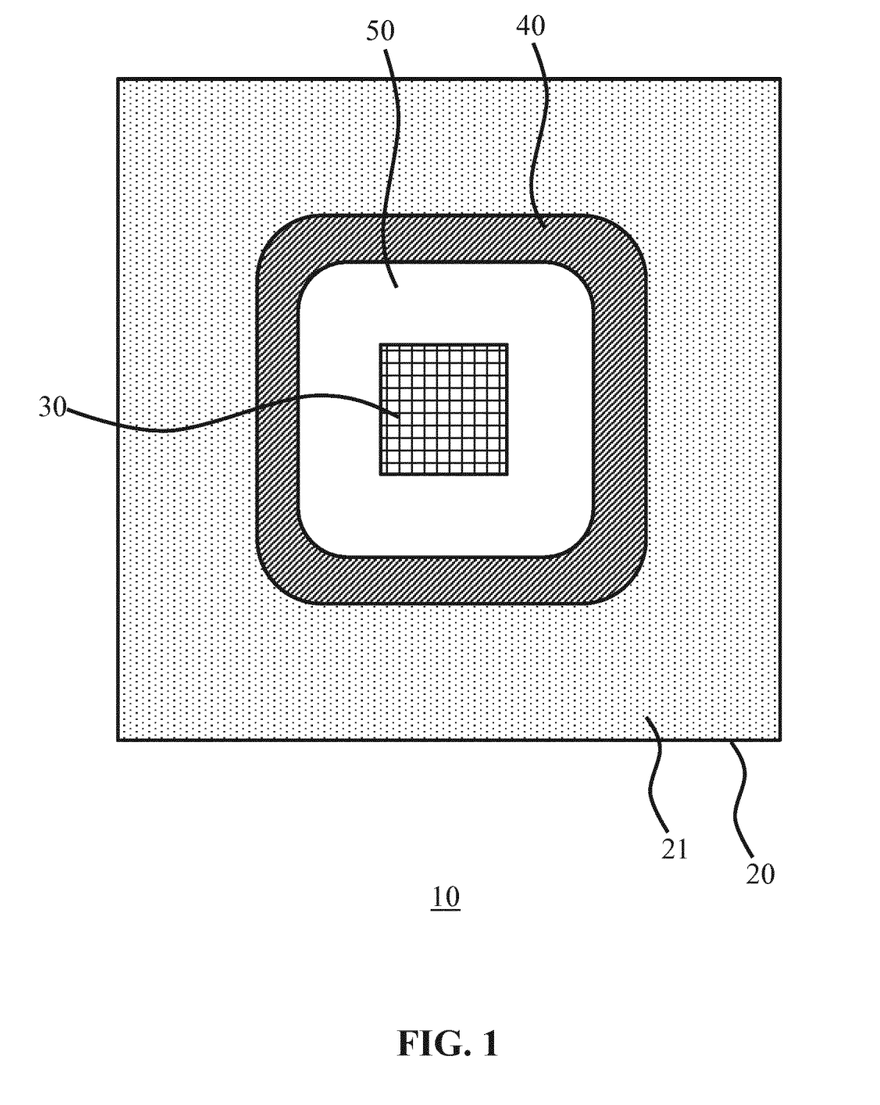
FIG. 1 schematically depicts a face-on view of a wearable patch according to an embodiment.
Figure 2:
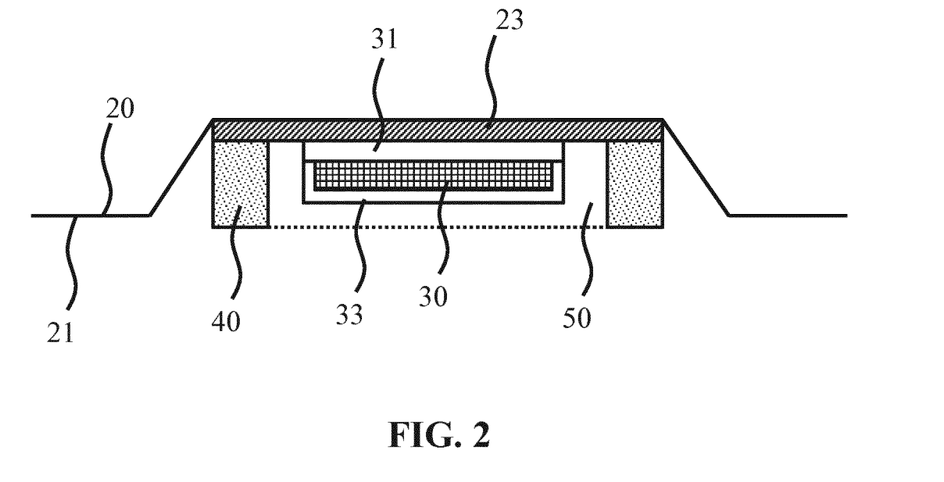
FIG. 2 schematically depicts a face-on view of a wearable patch according to another embodiment.

FIG. 1 schematically depicts a face-on view and FIG. 2 schematically depicts a cross-sectional view of a wearable patch 10 according to an embodiment of the present invention. The wearable patch 10 comprises an adhesive carrier 20 such as a tape, plaster, or the like, onto which an arrangement including an ultrasound transducer 30 is adhered in a central region of the adhesive carrier 20. It shall be understood by the person skilled in the art that the ultrasound transducer 30 may be either permanently or reversibly mounted on the patch. In the latter example (which is not illustrated), the adhesive carrier may have an opening through which the ultrasound transducer 30 can be placed and removed.

The outer region of the adhesive carrier 20 surrounding this central region also carries an adhesive 21 at least on a patient-facing surface such that when the wearable patch 10 is adhered to a skin region of the patient, the ultrasound waves-emitting surface of the ultrasound transducer 30 faces this skin region. Any suitable adhesive 21 may be used for this purpose. Examples of such suitable adhesives include silicone, acrylic, rubber, polyurethane and hydrocolloid based adhesives.

The ultrasound transducer 30 may comprise one or more ultrasound transducer cells arranged in a one-dimensional or two-dimensional array of transducer cells or elements, such as a 4×4 mm array having 16 ultrasound transducer elements with a pitch in a range of 200-300 microns, by way of non-limiting example. Other dimensions are of course equally feasible. In an embodiment, the ultrasound transducer elements are operable in a frequency range of 2-12 MHz, although other frequency ranges may be contemplated. Any suitable type of ultrasound transducer elements may be used for this purpose, e.g. piezoelectric transducer (PZT) elements, capacitive micro-machined ultrasound transducer (CMUT) elements, piezoelectric micro-machined transducer (PMUT) elements, and so on, although CMUT elements are particularly preferred, in particular over (PZT) elements due to their superior (adjustable) resonance frequency range, which make CMUT elements particularly suitable for patient monitoring purposes. As such transducer elements are well-known per se, they will not be explained in further detail for the sake of brevity only. The array of transducer cells may be arranged as a phased array to facilitate beam steering of an ultrasound beam generated with the ultrasound transducer 30. Again, such beam steering is well-known per se and will not be explained in further detail for the sake of brevity only.

The ultrasound transducer 30 typically is operable in a transmit mode in which the ultrasound beams are generated and a receive mode in which the ultrasound transducer 30 is operable to receive echo signals induced by the generated ultrasound beams within the body of the individual wearing the wearable patch 10. It shall be understood by the skilled in the art person that the disclosed herein wearable patch address a need of providing a reliable acoustic contact of any type of ultrasound transducers to be affixed to the skin of a patient for a longer period of time. The ultrasound transducer might have any type of functionality leveraging from ultrasound transmission and/or reception into/from the body of the patient.

The ultrasound transducer 30 may be mounted on a substrate 31, e.g. a chip or the like, onto which the ultrasound transducer 30 is manufactured. Such a substrate 31 may be made of any suitable material, such as a flex substrate, silicon substrate, a silicon on insulator substrate, a glass substrate, and so on. The ultrasound transducer elements of the ultrasound transducer 30 may be mounted on a backing material, which backing material may be mounted on the substrate 31. The substrate 31 may be secured against the adhesive carrier 20 using an intermediate carrier 23, e.g. a flex foil, PCB or the like in any suitable manner, e.g. using an adhesive, stud bonding, and so on. To allow a reversible fixation of the ultrasound transducer 30 to the patch the intermediate carrier 23 may have an opening, through which the ultrasound transducer 30 (and corresponding acoustic arrangement such as backing) can be placed and removed. The same opening can also serve for gel's disposal. An acoustic window material 33 may be applied over the patient-facing surface of the ultrasound transducer 30 to provide acoustic impedance matching of the ultrasound transducer cells of the ultrasound transducer 30 to the skin of the patient. Such acoustic window materials may be silicone-based, and may include particle fillers, e.g. metal oxide particles such as $Fe_2O_3$ or $SiO_2$ particles for impedance matching purposes. Other suitable acoustic window materials include layer stacks including a soft layer of silicone or polybutadiene rubber, covered by a layer of TPX (polymethyl pentene), PEBA (polyether block amide) or filled silicone. Other suitable acoustic window materials are well-known per se and will be immediately apparent to the skilled person.

Surrounding the ultrasound transducer 30 is arranged a seal ring 40 that defines a fluid reservoir 50 delimited by the seal ring 40 and the wearable patch 10. Therefore, a volume of the fluid reservoir 50 is defined by the seal ring, part of the patient's body surrounded by this ring, once the patch is secured to the patient's body, and a part of the patch (such as the intermediate carrier 23 in this example) opposing the patient's body part surrounded by ring. The seal ring is shown to have a rectangular closed outline by way of non-limiting example only as it should be understood that the seal ring may have any suitable closed shape, e.g. a circular shape. The seal ring 40 may extend from the intermediate carrier 23, as is shown by way of non-limiting example in FIG. 2. The seal ring 40 may be secured against the intermediate carrier 23 in any suitable manner, such as using an adhesive, e.g. glue or double-sided tape. The fluid reservoir 50 includes the ultrasound transducer 30 and has the purpose of containing a coupling agent such as an ultrasound conductive gel, which coupling agent can spread over the patient-facing surface of the ultrasound transducer 30 such that upon application of the wearable patch 10 to a skin region of the patient an acoustic coupling between the patient-facing surface of the ultrasound transducer 30 and the skin region of the patient is provided by the coupling agent. As will be explained in further detail below, the seal ring 40 comprises a plurality of fluid conduits (not shown in FIG. 1) into which access coupling agent can be evacuated when applying downward pressure onto the wearable patch 10 when positioning the wearable patch 10 onto the skin region of the patient.

Figure 3:
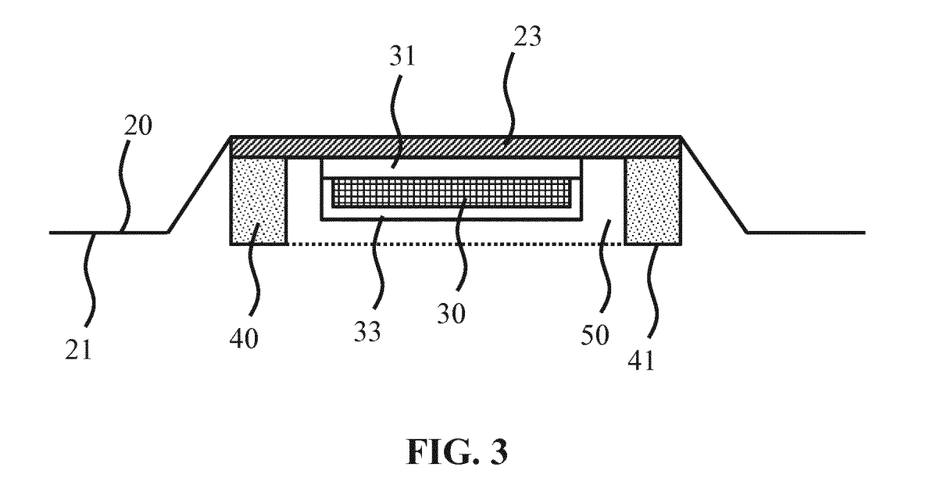
FIG. 3 schematically depicts a cross-sectional view of a wearable patch according to an embodiment.

FIG. 3 schematically depicts a cross-sectional view of an alternative embodiment of the wearable patch 10, in which the patient-facing surface of the seal ring 40 also carries an adhesive 41 for adhering the wearable patch 10 to the patient. Such an adhesive 41 may be the same adhesive as the adhesive 21 or may be a different adhesive. Alternatively, the adhesive 21 may be omitted when the adhesive 41 is present. The adhesive 21 and/or the adhesive 41 in any of the aforementioned embodiments may be a pressure sensitive adhesive that forms a bond with the skin region of the patient when pressure is applied to the wearable patch 10. Such a pressure sensitive adhesives typically are based on the elastomer compounded with a suitable tackifier such as a rosin ester. Any suitable elastomer such as for example, an acrylic, rubber, nitrile, silicone rubber, styrene block copolymer and so on may be used for this purpose. Of course, the adhesive 21 and/or the adhesive 41 does not need to be a pressure sensitive adhesive but instead may be any suitable permanent adhesive as will be readily understood by the skilled person.

Figure 4:
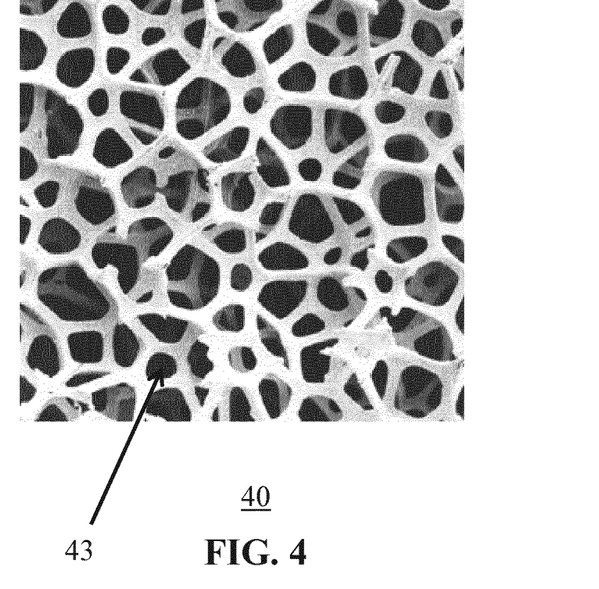
FIG. 4 schematically depicts a cross-sectional view of a wearable patch according to another embodiment.

FIG. 4 schematically depicts a cross-sectional view of the seal ring 40 according to a first set of embodiments of the present invention. In this embodiment, the seal ring 40 is made of a porous material in which the pores 43 of the porous material define the fluid conduits through the seal ring 40. As previously explained, the seal ring 40 preferably is made of a flexible material such that the seal ring 40 can be compressed when the wearable patch 10 is pressed against the skin region of the patient (contacting the part of the patient's body (skin), when the wearable patch is secured to said part of the patient's body), thereby forming a hermetic seal between the wearable patch 10 and the skin region such that the fluid reservoir 50 is sealed off apart from the fluid conduits, e.g. the pores 43 of the seal ring 40 into which the coupling agent in the fluid reservoir 50 can expand upon exertion of pressure on the wearable patch 10. The pores 43 may be open pores, i.e. pores that define a conduit that extends through the entirety of the seal ring 40 such that the fluid reservoir 50 is in fluid communication with the outside world through the pores 43. Alternatively, the pores 43 may be closed pores, i.e. pores that terminate within the seal ring 40. In such an embodiment, the pores 43 may still act as fluid storage compartments for the access coupling agent in the fluid reservoir 50, although air such as from air bubbles cannot escape the fluid reservoir 50 through the pores 43. Hence, in this embodiment it is preferred that the seal ring 40 further comprises at least one vent channel (not shown) extending through the entirety of the seal ring 40 to allow such air to escape from the fluid reservoir 50. Such a vent channel may be formed through the seal ring 40 in any suitable manner, e.g. through etching, (laser) drilling, cutting, and so on.

In a preferred embodiment, the porous seal ring 40 is made of a foam, more preferably a compressible foam such as for example polymer foams including but not limited to polyurethane, polystyrene, polyethylene, silicone and polyvinylchloride.

Figure 5:
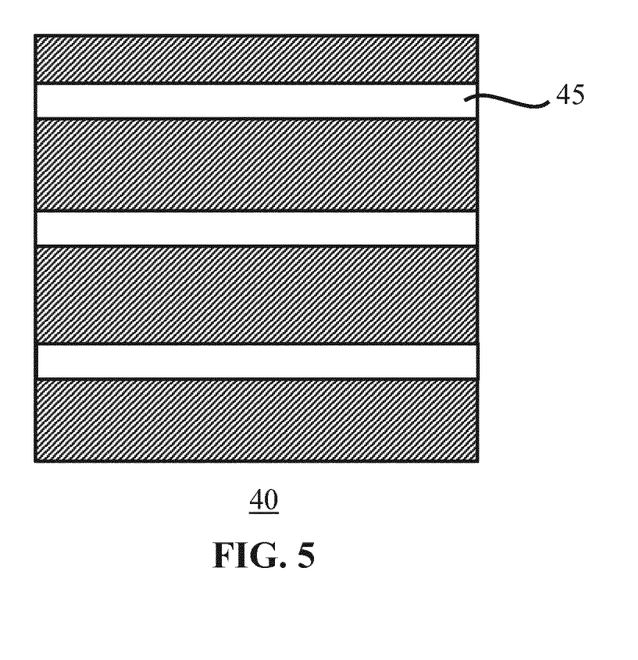
FIG. 5 schematically depicts a cross-sectional view of a seal ring of a wearable patch according to an embodiment.

FIG. 5 schematically depicts a cross-sectional view of the seal ring 40 according to a first set of embodiments of the present invention. In this embodiment, the seal ring 40 is made of a non-porous material, in which the fluid conduits 45, e.g. vent channels, are formed through the through the seal ring 40 in any suitable manner, e.g. through etching, (laser) drilling, cutting, and so on. Suitable seal ring materials include but are not limited to thermoplastic elastomers, elastomers, (nitrile-, butadiene-, butyl-) rubbers, polyurethanes and silicones.

Figure 6:
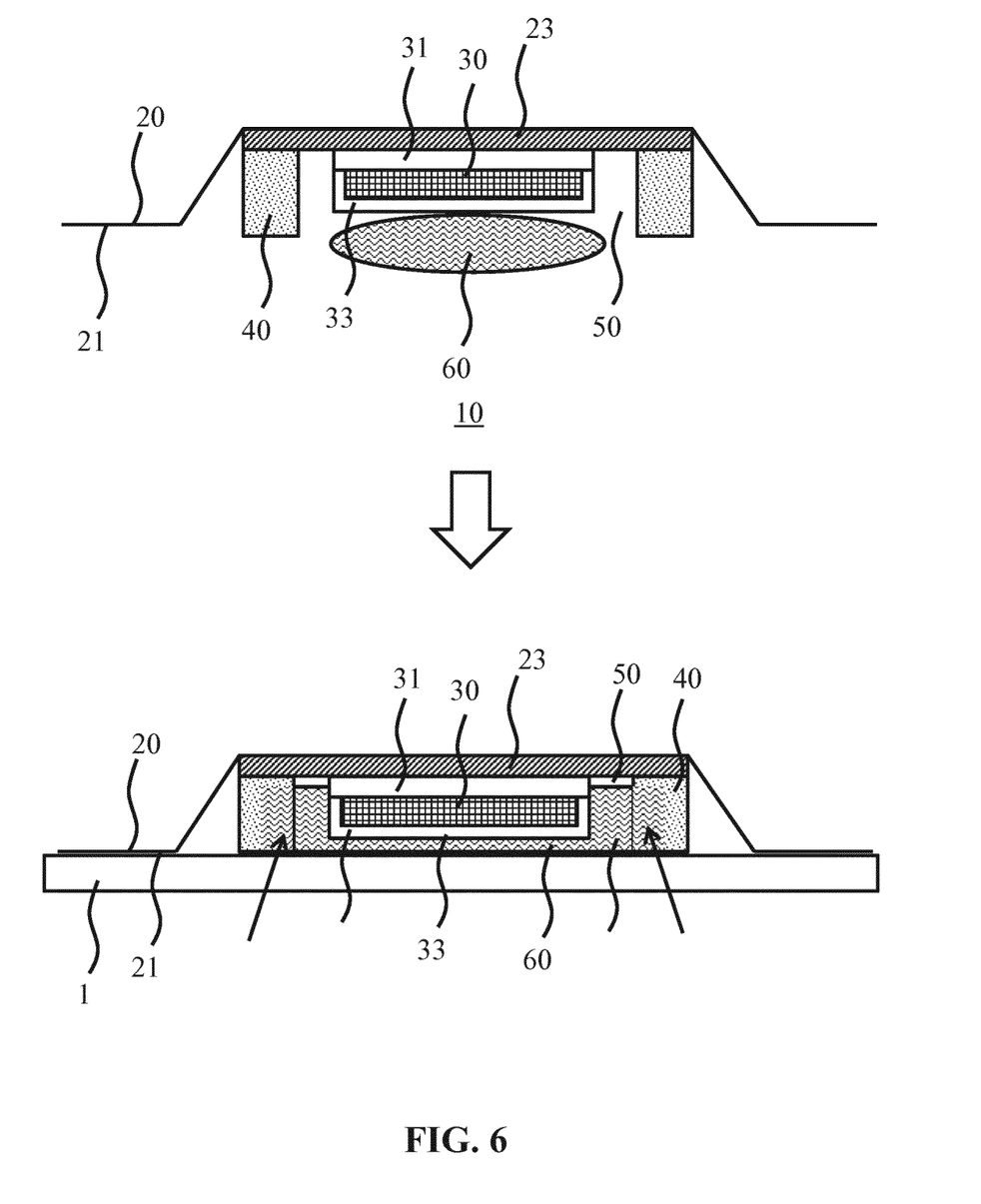
FIG. 6 schematically depicts a cross-sectional view of a seal ring of a wearable patch according to another embodiment.

FIG. 6 schematically depicts the steps of a method of applying the wearable patch 10 to a skin region 1 of a patient. In a first step, a coupling agent 60 is applied to the fluid reservoir 50 after which the wearable patch 10 is applied to the skin region 1. During this application, pressure may be exerted onto the wearable patch 10, which reduces the effective volume of the fluid reservoir 50 such that the coupling agent 60 substantially fills the fluid reservoir 50 and access coupling agent 60 is forced into the fluid conduits of the seal ring 50 as schematically depicted by the arrows in the bottom pane of FIG. 6. Where the amount of pressure exerted onto the wearable patch 10 is varied, the effective thickness of the layer of coupling agent 60 in between the ultrasound transducer 30 and the skin region 1 can vary due to the fluid communication between the fluid reservoir 50 and the fluid conduits in the seal ring 40. Typically an increase in this pressure will cause the effective thickness of this layer to reduce as more coupling agent 60 is forced into the seal ring 40, whereas a reduction in this pressure will cause the effective thickness of this layer to increase as coupling agent 60 flows back into the fluid reservoir 50 from the fluid conduits in the seal ring 40.

Importantly, air bubbles that are forced into the fluid conduits of the seal ring 40 by the application of such a pressure onto the wearable patch 10 tend to remain in the seal ring 40 even when such a pressure is reduced due to the fact that such air bubbles typically have a lower surface energy in the fluid conduits of the seal ring 40. Such air bubbles may have an approximately round shape in the fluid conduits, e.g. pores 43, of the seal ring 40 whereas such air bubbles adopt a more ellipsoid (pancake-like) shape in the fluid reservoir 50, i.e. a shape having a higher surface energy, in particular where such bubbles are located in between the patient-facing surface of the ultrasound transducer 30 and the opposing region of the patient's skin.

Furthermore, the excess coupling agent 60 that is forced into the fluid conduits of the seal ring 40 effectively seals off the volume of the coupling agent 60 within the fluid reservoir 50 from exposure to ambient air as this excess coupling agent 60 fills the fluid conduits, thereby preventing ambient air from reaching the fluid reservoir 50. Consequently, the coupling agent 60 within the fluid reservoir 50 is protected against dehydration or drying out, such that the coupling agent 60 within the fluid reservoir 50 retains its desired properties over a prolonged period of time, i.e. the period of time during which the wearable patch 10 has to be worn by the patient.

A further advantage of applying a wearable patch 10 according to at least some embodiments of the present invention is that the wearable patch 10 may be positioned on an initial skin region 1 of the patient without having to affix, e.g. adhere, the wearable patch 10 to the patient. This facilitates checking whether the wearable patch 10 is positioned in the correct skin region 1 of the patient by acquiring one or more ultrasound images with the ultrasound transducer 30, which images may be evaluated, e.g. by a medical professional, in order to check if the wearable patch 10 is optimally positioned. In case of non-optimal positioning of the wearable patch 10, such one or more ultrasound images may provide guidance to the medical professional on how to readjust the position of the wearable patch 10 on the skin of the patient in order to ensure that the wearable patch 10 is optimally positioned, after which the wearable patch 10 may be affixed to the patient. Due to the fact that the coupling agent 60 is at least in part stored in the fluid conduits within the seal ring 40, such repositioning of the wearable patch 10 can be done by simply sliding or otherwise moving the wearable patch 10 across the skin of the patient without the need to reapply the coupling agent 60 to the ultrasound transducer 30.

Figure 7:
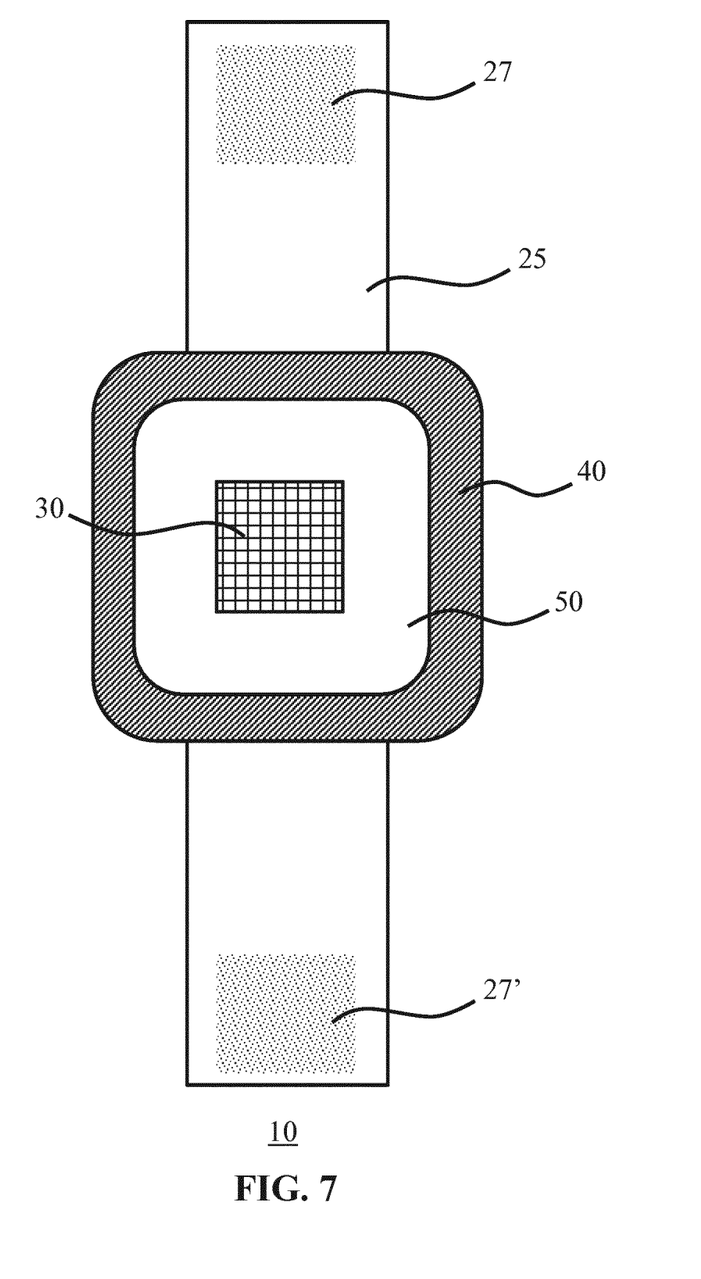
FIG. 7 schematically depicts the application of a wearable patch according to an embodiment to a skin region of a patient.

FIG. 7 schematically depicts a face-on view of a wearable patch 10 according to another embodiment of the present invention. In this embodiment, the wearable patch 10 may be secured against a body portion of the patient using a strap 25 having a fixing arrangement including a first fixing member 27 and a second fixing member 27', which fixing members are adapted to engage with each other in order to close the strap 25 and secure the wearable patch 10 against the patient's body in this manner. For example, such a fixing arrangement may comprise a buckle 27 and a plurality of holes 27' for receiving the locking pin of the buckle 27. Alternatively, such a fixing arrangement may be a Velcro arrangement, in which the first fixing member 27 embodies the hooks of the Velcro arrangement and the second fixing member 27' embodies the loops of the Velcro arrangement. Other fixing arrangements, e.g. a button arrangement, a push button arrangement, a zip arrangement, an adhesive arrangement, and so on may be contemplated for securing the strap 25 against the body of the patient. Further embodiments of the wearable patch 10 may include a combination of the adhesive layer 20 and the strap 25 to provide a particularly secure fastening of the wearable patch 10 against a skin region of the patient.

The wearable patch 10 according to embodiments of the present invention may be provided together with a container comprising a coupling agent 60, e.g. a bottle of ultrasound conductive gel or the like to form a wearable patch kit 10 according to embodiments of the present invention.

Figure 8:
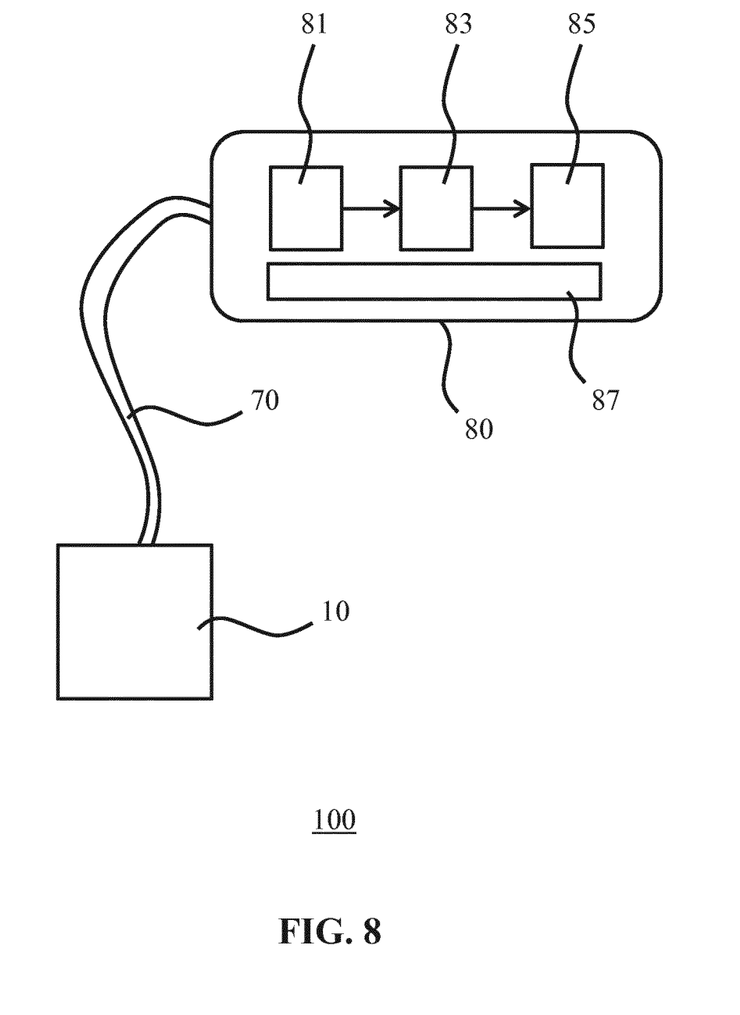
FIG. 8 schematically depicts a wearable patch assembly according to an embodiment.

FIG. 8 schematically depicts a wearable patch assembly 100 comprising the wearable patch 10 according to embodiments of the present invention and a control module 80 for controlling the ultrasound transducer 30. The control module 80 may be connected to the ultrasound transducer 30 through a wire or cable 70, which may be any suitable wire or cable, e.g. a coaxial cable, a cable comprising individually insulated wires, a ribbon comprising conductive tracks, and so on. In an alternative embodiment the control module can be coupled to the transducer wirelessly. The control module 80 may comprise circuitry 81 for controlling the ultrasound transducer 30. For example, the circuitry 81 may include an array controller coupled to a down conversion stage, which may form part of the array controller or may be a separate entity. The down conversion stage may apply noise filtering and frequency down conversion of the echo signals, e.g. from the MHz domain to the KHz domain, and employ a signal envelope to the down converted echo signals to reduce the amount of data that needs to be provided to a signal processor for deriving the desired bladder information from the acquired echo signals. Other suitable data reduction techniques will be immediately apparent to the skilled person.

The circuitry 81 may further comprise a signal processor for processing the signals received from the ultrasound transducer 30. Alternatively, such a signal processor may form part of a remote device, e.g. a wearable smart device such as a smart watch, a portable smart device such as a mobile phone or tablet computer, a laptop computer, a personal computer, or the like in order to reduce the computational effort required from the wearable patch 10 such that the lifetime of the battery 87 within the control module 80 may be extended.

The circuitry 81 may be communicatively coupled to a data storage device 83, e.g. a memory or the like, on-board the control module 80, with a wireless communication module 85 communicatively coupled to the data storage device 83 such that the data pertaining to the acquired echo signals as stored in the data storage device 83 may be periodically communicated to a remote device, e.g. in response to a communication request from the remote device. Any suitable wireless communication protocol, e.g. Bluetooth, Wi-Fi, a mobile communication protocol such as 3G, 4G, 5G or the like, a near field communication protocol (NFC), and so on, may be deployed for the communication between the control module 80 and the remote device.

As mentioned previously, the data pertaining to the acquired echo signals communicated from the control module 80 to such a remote device preferably is reduced in size to minimize the amount of data that needs to be communicated in this manner in order to extend the lifetime of the battery 87. It should be understood that in alternative embodiments in which the circuitry 81 comprises the signal processor, the wireless communication module 85 may be used to communicate a processing result of the signal processor to such a remote device, e.g. for visualization of the processing result on a display of the remote device. In an alternative embodiment both the wearable patch 10 and the control module 80 can be housed in the same housing.

In yet a further embodiment, the control module 80 is configured to upload the data pertaining to the acquired echo signals with a wireless communication module 85 into a remote data repository acting as an intermediary data storage device from which the remote device may download the stored data. This has the advantage that the remote device does not have to be within communication range of the wireless communication module 85 but instead may download the data at any suitable point in time to evaluate this data. For example, the remote data repository may be a cloud storage solution or the like, which may be accessed by both the wireless communication module 85 and the remote device over a network connection such as the Internet, in which case the wireless communication module 85 may establish a wireless connection with an Internet hub such as a router or the like within communication range of the wireless communication module 85 through which the data pertaining to the acquired echo signals may be uploaded into the remote data repository.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A wearable patch suitable for receiving an ultrasound transducer to be mounted on the patch, said patch comprising:
   a seal ring adapted to surround the ultrasound transducer, when it is mounted on the patch and arranged to be in contact with a part of a patient's body, when the wearable patch is secured to said part of the patient's body; and
   a fluid reservoir for containing a coupling agent for the ultrasound transducer when the wearable patch is secured to said part of the patient's body, said fluid reservoir being delimited by a portion of the patch, the seal ring and said part of the patient's body, and
   wherein said seal ring comprises a plurality of fluid conduits extending from the fluid reservoir at least partially through the seal ring, wherein the seal ring is made of a porous material, the pores of said porous material defining the plurality of fluid conduits, wherein said pores are closed pores, and wherein the seal ring further comprises at least one vent channel extending from the fluid reservoir through the seal ring, wherein the seal ring is flexible, and wherein the effective volume of the fluid reservoir is reducible, when the wearable patch is secured to the patient's body, by applying pressure to the wearable patch, thereby compressing the seal ring.

2. The wearable patch of claim 1 further comprising the ultrasound transducer.

3. The wearable patch of claim 1, wherein the seal ring is made of a porous foam.

4. The wearable patch of claim 3, wherein the porous foam is selected from polyurethane, polystyrene, polyethylene, silicone and polyvinylchloride.

5. The wearable patch of claim 1, wherein the patch has a central region carrying the ultrasound transducer and the seal ring, and an outer region surrounding the central region, wherein at least the outer region carries an adhesive.

6. The wearable patch of claim 1, wherein a surface portion of the seal ring for contacting the skin of a wearer of the patch carries an adhesive.

7. The wearable patch of claim 5, wherein the adhesive is a pressure-sensitive adhesive.

8. The wearable patch of claim 1, further comprising a strap for securing the patch to a part of a patient's body.

9. A wearable patch assembly comprising the wearable patch according to claim 1 and a control module coupleable to the ultrasound transducer through either one of a cable and a wire or wirelessly, said control module comprising circuitry for controlling the operation of the ultrasound transducer and/or for processing the ultrasound images captured with the ultrasound transducer.

10. A method of applying the wearable patch of claim 1 to a skin region of a patient, the method comprising:
    filling the fluid reservoir of the wearable patch with a coupling agent;
    positioning the wearable patch onto the skin region; and
    applying pressure to the wearable patch such that the seal ring contacts a part of a patient's body thereby reducing the effective volume of the fluid reservoir causing air bubbles and excess coupling agent in the fluid reservoir to be forced into the plurality of fluid conduits.

11. The method of claim 10, further comprising:
    mounting the ultrasound transducer on the wearable patch;
    capturing at least one image with the ultrasound transducer positioned on said skin region; and
    adjusting said positioning based on the captured at least one image.

* * * * *